US010144547B2

(12) United States Patent
Enos et al.

(10) Patent No.: US 10,144,547 B2
(45) Date of Patent: Dec. 4, 2018

(54) MEDICAL LABELING APPARATUS WITH DRUG INFORMATION

(71) Applicant: CODONICS, INC., Middleburg Heights, OH (US)

(72) Inventors: Gary Enos, Hudson, OH (US); Lawrence Srnka, Northfield Center, OH (US)

(73) Assignee: CODONICS, INC., Middleburg Heights, OH (US)

( * ) Notice: Subject to any disclaimer, the term of this patent is extended or adjusted under 35 U.S.C. 154(b) by 0 days.

(21) Appl. No.: 15/543,417

(22) PCT Filed: Jan. 15, 2016

(86) PCT No.: PCT/US2016/013555
§ 371 (c)(1),
(2) Date: Jul. 13, 2017

(87) PCT Pub. No.: WO2016/122907
PCT Pub. Date: Aug. 4, 2016

(65) Prior Publication Data
US 2018/0002056 A1  Jan. 4, 2018

Related U.S. Application Data

(60) Provisional application No. 62/103,950, filed on Jan. 15, 2015.

(51) Int. Cl.
*B65C 9/46* (2006.01)
*G06F 17/40* (2006.01)
(Continued)

(52) U.S. Cl.
CPC .................. *B65C 9/46* (2013.01); *B65C 1/00* (2013.01); *G06F 17/40* (2013.01); *G06F 19/00* (2013.01);
(Continued)

(58) Field of Classification Search
CPC .. G06F 19/3462; G06F 19/322; G06F 19/326; G06F 19/3406; G06F 19/3456;
(Continued)

(56) References Cited

U.S. PATENT DOCUMENTS 5,797,515 A * 8/1998 Liff ..................... G06F 19/3462
221/129
5,883,370 A * 3/1999 Walker ................ G06F 19/3462
235/375

(Continued)

OTHER PUBLICATIONS

PCT International Search Report and Written Opinion from PCT International Application No. PCT/US2016/013555, International Filing Date Jan. 15, 2016 (6 pgs).

*Primary Examiner* — Fekadeselassie Girma
(74) *Attorney, Agent, or Firm* — Kraguljac Law Group, LLC

(57) ABSTRACT

Provided is a labeling apparatus that generates a label for labeling a drug container at a healthcare facility. The labeling apparatus includes a code reader that reads a computer-readable code encoding a drug to be stored by the drug container and transmits a signal indicative of the identity of the drug in response to reading the computer-readable code. A non-transitory computer-readable memory stores a drug formulary comprising a plurality of drug entries. A processing component is configured to identify, from the formulary, the identity of the drug corresponding to the computer-readable code and receives a patient identity from a computer-accessible source. A printer is operable to print label content identifying the specific drug onto a label that is to be applied to the drug container. The label content includes the identity of the drug and the patient identity encoded by a label code that is computer-readable.

8 Claims, 6 Drawing Sheets

(51) Int. Cl.
*A61M 5/14* (2006.01)
*B65C 1/00* (2006.01)
*G09F 3/00* (2006.01)
*G06F 19/00* (2018.01)
*G06K 7/10* (2006.01)
*G08B 21/02* (2006.01)
*G16H 20/10* (2018.01)
*A61M 5/145* (2006.01)

(52) U.S. Cl.
CPC ...... *G06F 19/3456* (2013.01); *G06F 19/3462* (2013.01); *G06K 7/10712* (2013.01); *G08B 21/02* (2013.01); *G09F 3/00* (2013.01); *G16H 20/10* (2018.01); *A61M 5/14546* (2013.01); *A61M 2205/18* (2013.01); *A61M 2205/6009* (2013.01); *A61M 2205/6072* (2013.01)

(58) Field of Classification Search
CPC .. G06F 17/30247; G06F 19/30; G06F 19/366; G06F 3/1203; G06F 3/1243; G06F 3/1256; G06Q 50/22; G06Q 50/24; G07F 17/0092; G07F 11/002; A61J 1/03; A61J 2205/30; A61J 2205/10; A61J 2205/60; A61J 7/0084; G09F 2003/0272; G09F 2003/0273; G09F 3/00; A61M 2005/14208; A61M 2205/18; A61M 2205/33; A61M 2205/3334; A61M 2205/50; B41J 3/4075; B65B 3/003; B65C 9/46; G01N 2035/00861; G06K 9/18

See application file for complete search history.

(56) References Cited

U.S. PATENT DOCUMENTS

| | | | | |
|---|---|---|---|---|
| 5,963,136 A * | 10/1999 | O'Brien | ............... | A61J 7/0481 340/573.1 |
| 6,529,801 B1 * | 3/2003 | Rosenblum | ......... | G06F 19/3462 700/232 |
| 7,448,544 B1 * | 11/2008 | Louie | ............... | G06F 19/3462 235/385 |
| 8,120,489 B2 * | 2/2012 | Hatanaka | ............... | G06Q 10/06 340/572.4 |
| 8,146,747 B2 * | 4/2012 | Luciano, Jr. | ........ | G06F 19/3462 206/459.5 |
| 8,224,664 B1 * | 7/2012 | Louie | ................... | G06Q 10/083 705/2 |
| 9,098,861 B2 * | 8/2015 | Ban | ........ | G06Q 30/02 |
| 9,245,304 B2 * | 1/2016 | Luciano, Jr. | ............ | G06Q 50/22 |
| 9,524,376 B2 * | 12/2016 | Hoover | ................ | G06F 3/1243 |
| 9,798,861 B2 * | 10/2017 | Adler | ................ | G06F 19/3462 |
| 2002/0173875 A1 * | 11/2002 | Wallace | ................ | G06F 19/322 700/242 |
| 2003/0174326 A1 * | 9/2003 | Rzasa | ....................... | G01J 3/02 356/326 |
| 2003/0189732 A1 * | 10/2003 | Bean | ........................ | A61J 1/03 358/302 |
| 2003/0216831 A1 * | 11/2003 | Hart | ....................... | G06F 19/322 700/235 |
| 2006/0060645 A1 * | 3/2006 | Udaka | ................ | G06F 19/3462 235/375 |
| 2006/0163103 A1 * | 7/2006 | Adler | ....................... | A61J 1/00 206/459.5 |
| 2007/0204497 A1 * | 9/2007 | de la Huerga | ...... | G06F 19/3462 40/630 |
| 2008/0030309 A1 * | 2/2008 | Darrouzet | ................ | A61J 7/04 340/309.7 |
| 2008/0077439 A1 * | 3/2008 | Guion | ................ | G06Q 10/109 705/2 |
| 2008/0288287 A1 * | 11/2008 | Stanners | ............... | G06F 19/326 705/2 |
| 2008/0303638 A1 * | 12/2008 | Nguyen | ............... | G06F 19/3462 340/10.42 |
| 2010/0031611 A1 * | 2/2010 | Ali | ....................... | G06F 19/3462 53/467 |
| 2010/0145506 A1 * | 6/2010 | Waugh | ................ | G06F 19/3462 700/231 |
| 2012/0089411 A1 * | 4/2012 | Srnka | ..................... | G06Q 50/22 705/2 |
| 2013/0110516 A1 * | 5/2013 | Abulhaj | ................ | G10L 21/00 704/274 |
| 2013/0327822 A1 * | 12/2013 | Keefe | ....................... | G06F 17/40 235/375 |
| 2014/0058555 A1 * | 2/2014 | Rhoads, Jr. | ......... | G06F 19/3462 700/215 |
| 2014/0288947 A1 * | 9/2014 | Simpson | ............. | G06F 19/3418 705/2 |
| 2015/0261934 A1 * | 9/2015 | Miller | ................ | G06F 19/3456 705/3 |
| 2016/0132659 A1 * | 5/2016 | Vaz | ................... | G06F 19/3462 700/242 |
| 2016/0247277 A1 * | 8/2016 | Kriheli | ................... | B65B 55/02 |
| 2016/0267229 A1 * | 9/2016 | High | ................... | G06F 19/326 |

* cited by examiner

MEDICAL LABELING APPARATUS WITH DRUG INFORMATION

BACKGROUND OF THE INVENTION

1. Field of the Invention

This application relates generally to a labeling apparatus for generating labels and, more particularly, a labeling apparatus and method for generating labels including a machine-readable code to be applied to drug containers in a medical environment.

2. Description of Related Art

Conventional labeling systems suffer from many drawbacks, and have limited reliability due primarily to human error. Sloppy handwriting can make the label difficult to read, or altogether illegible. Each technician who prepares such a label may also do so in a different manner, or attribute different meanings to the content of a label than another technician. In such situations, the label content is left open to interpretation, and often lacks information essential for proper documentation and record keeping purposes.

Further, conventional labeling systems generally lack the ability to generate labels that are useful to facilitate a secure double check that the proper patient is to receive a drug to be administered via an automated drug delivery device. Traditionally, human-readable label content was manually compared to other human-readable content identifying the patient at the location where the drug is to be administered to the patient.

BRIEF SUMMARY OF THE INVENTION

According to one aspect, the subject application involves a labeling apparatus that generates a label for labeling a drug container at a healthcare facility. Such a labeling apparatus includes a code reader that reads a computer-readable code encoding a drug to be stored by the drug container and transmits a signal indicative of the identity of the drug in response to reading the computer-readable code. A non-transitory computer-readable memory stores a drug formulary comprising a plurality of drug entries. A processing component is configured to identify, from the formulary, the identity of the drug corresponding to the computer-readable code and receives a patient identity from a computer-accessible source. A printer is operable to print label content identifying the specific drug onto a label that is to be applied to the drug container. The label content includes the identity of the drug and the patient identity encoded by a label code that is computer-readable.

According to another aspect, the subject application involves a method of administering a drug to a patient utilizing an automated drug delivery device. According to such a method, a computer-readable code reader is used to scan a drug code that is computer-readable and a first patient code that is also computer readable. The drug code and the first patient code are associated with a drug container storing the drug to be administered by the automated drug delivery device. With the computer-readable code reader, a second patient code that is computer readable and independent of the first patient code is scanned. A first patient identity determined based on the first patient code is compared to a second patient identity determined based on the second patient code to make a determination whether the first patient identity matches the second patient identity. The drug delivery device is configured to administer the drug to the patient in response to making a determination that the first patient identity matches the second patient identity, and an alert is initiated in response to making a determination that the first patient identity does not match the second patient identity.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
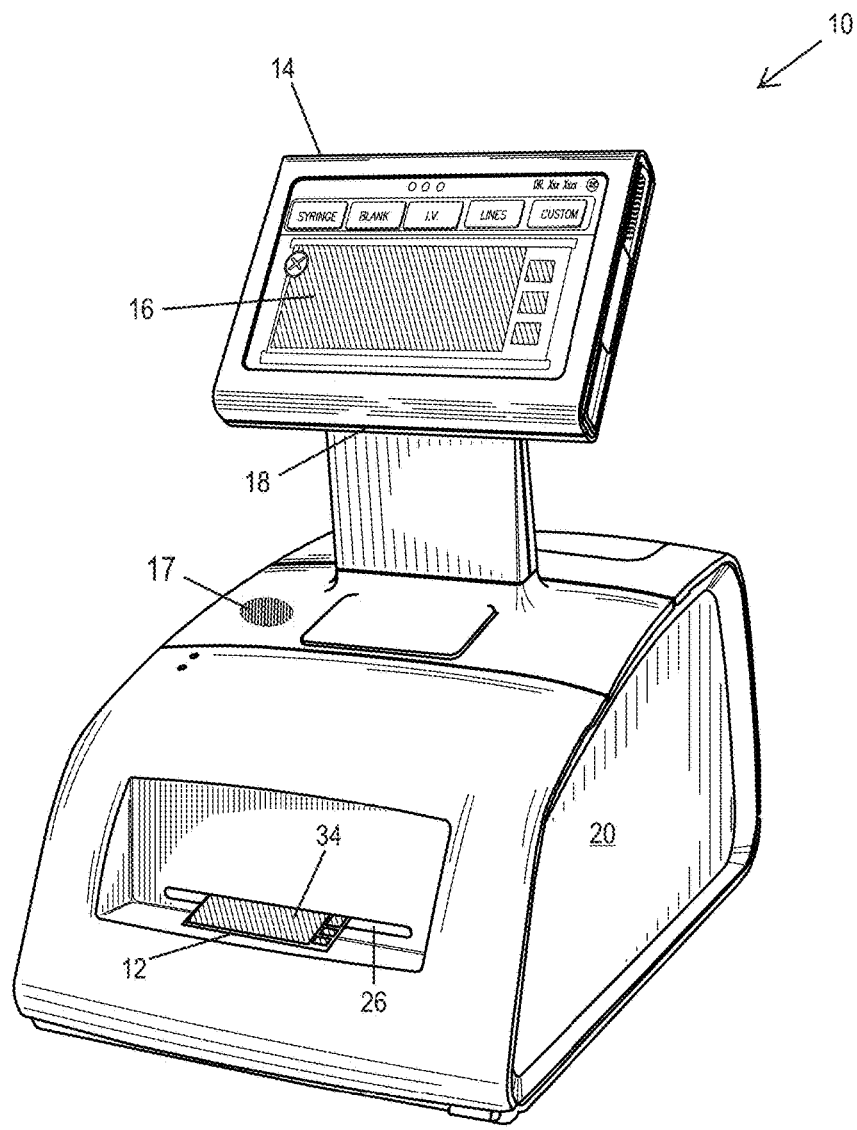
FIG. 1 shows an illustrative embodiment of a labeling apparatus for generating labels to be applied to medicinal substances in a medical facility.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

As shown in FIG. 1, the computer terminal 10 includes a touch-screen display 14 that can be pivotally coupled to a cabinet 20 to display a virtual label 16 comprising label content 34 that will be printed onto a label 12 that will be applied to a medicinal substance. The computer terminal 10 can be operable to scan a computer-readable code and print a label to be applied to a medical container such as a syringe as described in U.S. patent application Ser. No. 12/901,110, which is incorporated by reference herein in its entirety. The display 14 can display soft keys that, when touched by a technician or any other user, inputs data and commands into the computer terminal 10. The virtual label 16 is a computer-generated rendering of the label 12 that offers the user visual confirmation of the appearance of the physical label 12 to be printed by a printer 26. A computer-input peripheral such as a non-contact scanner 18, for example, can be provided at a convenient location, such as integrally formed in a bottom portion of the display 14 to read a machine-readable code supported beneath the scanner 18 for example. Integrally forming the scanner 18 as part of the display 14 provides for space savings over an arrangement where the scanner 18 is formed as a separate peripheral, which can be repositioned relative to the display 14. However, other embodiments can allow for a separate and distinct scanner 18 and/or display 14.

The computer-input peripheral can be a barcode reader or radio-frequency identification ("RFID") tag reader, or any other device that reads a machine-readable code such as a barcode or RFID code, respectively, or any other machine-readable code without requiring contact between the computer terminal and the code, and optionally the user during entry of the code. According to alternate embodiments, the display 14 can be utilized by a user as the computer-input peripheral. For such embodiments, the soft keys displayed by the display 14 can be selected to input information such as a medicinal substance being prepared to be administered to a patient or other information to be utilized in generating the label as described herein. According to yet alternate embodiments, a speaker 17 can optionally be provided to the display 14 or any other portion of the computer terminal 10 to broadcast audible sounds.

Figure 2:
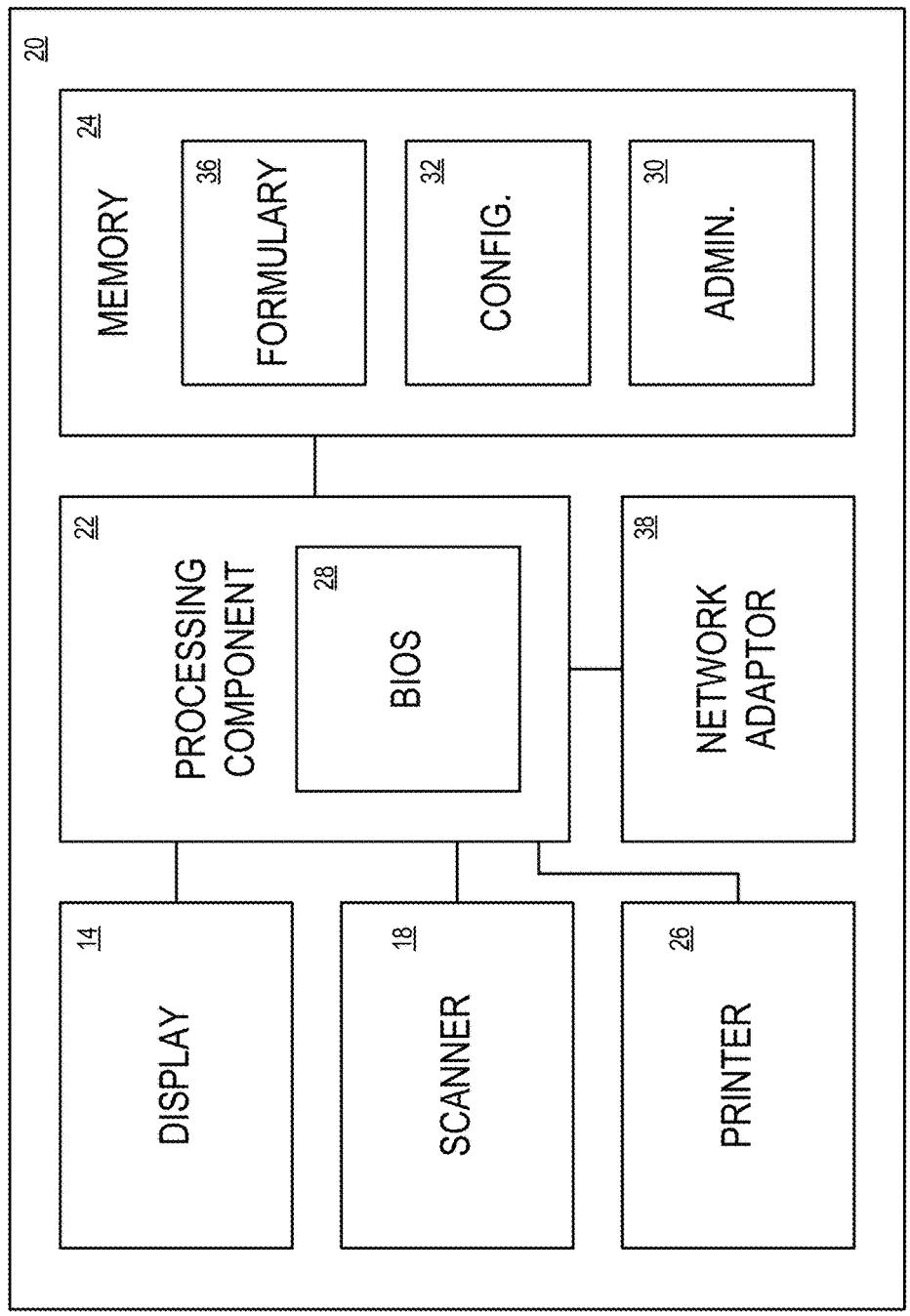
FIG. 2 shows a block diagram schematically depicting components of a labeling apparatus for generating labels to be applied to medicinal substances in a medical facility.

The computer terminal 10 also includes a cabinet 20 that houses or supports components that are operable to produce the label 12 in compliance with a medical labeling standard. But if what is being labeled is anything other than the medicinal substance, then the label 12 produced is to be compliant with a standard developed by a trade or professional organization, governing body, government agency, a healthcare provider or facility such as a hospital, or any other standards body setting forth policies for labeling such material. The internal components housed within the cabinet 20 are schematically illustrated by the block diagram of FIG. 2. The components can be formed from an arrangement of computer hardware such as ASICs, computer processors, programmable logic controllers and other circuitry; or a combination of computer hardware and computer-executable instructions. For example, a processing component 22 is provided to execute computer-executable instructions stored in a non-transitory, computer-readable memory 24 such as a hard disk drive, read-only memory ("ROM"), random access memory ("RAM"), optical disc, or any other suitable memory device, or any combination thereof. The computer-executed instructions, when executed by the computer processor 22, result in the performance of the method of generating a label for a medicinal substance described in detail below. A BIOS 28 is provided to load the operating system and other such administrative instructions 30 stored in the memory 24 and manage hardware interface permissions of the computer terminal 10. The operating system can be configured to only load authorized updates to prevent unauthorized changes to the formulary 36, configuration data 32 and administration instructions 30. Configuration data 32 controls various features of the computer terminal 10 that are active and available for use at any given time. The configuration data 32 can optionally be stored, updated and deleted from the memory 24 by the introduction of a so-called smart drive comprising a USB compatible flash memory to the computer terminal 10. When the smart drive is introduced to the computer terminal 10, it establishes the configuration data 32 of the computer terminal 10. The configuration data 32 can optionally be used to deactivate functional features that the computer terminal 10 would otherwise be able to perform based on the model of the computer terminal 10 purchased. Accordingly, a common hardware platform of the computer terminal 10 can be configured in a plurality of different functional configurations based on the configuration data 32.

In addition to the administrative instructions 30, the memory 24 also stores an updatable formulary 36 containing a database of medicinal substances that can be identified by the computer terminal 10 and select information for each medicinal-substance entry in the database. The formulary 36 can optionally be stored, updated and deleted from the memory 24 by the introduction of a so-called smart drive comprising a USB compatible flash memory to the computer terminal 10. When the smart drive is introduced to the computer terminal 10, it establishes the formulary 36 of the computer terminal 10. Illustrative examples of the select information that can be provided for the medicinal-substance entries includes, but is not limited to, an ID number such as a NDC code, UPC code, EAN code, or any other identifying data that can be used to relate a barcode or other computer-readable code to the medicinal-substance entries; a sound file that, when played, audibly announces the name of the medicinal substance identified in response to scanning a machine readable code; warning data; or any combination thereof.

Figure 3:
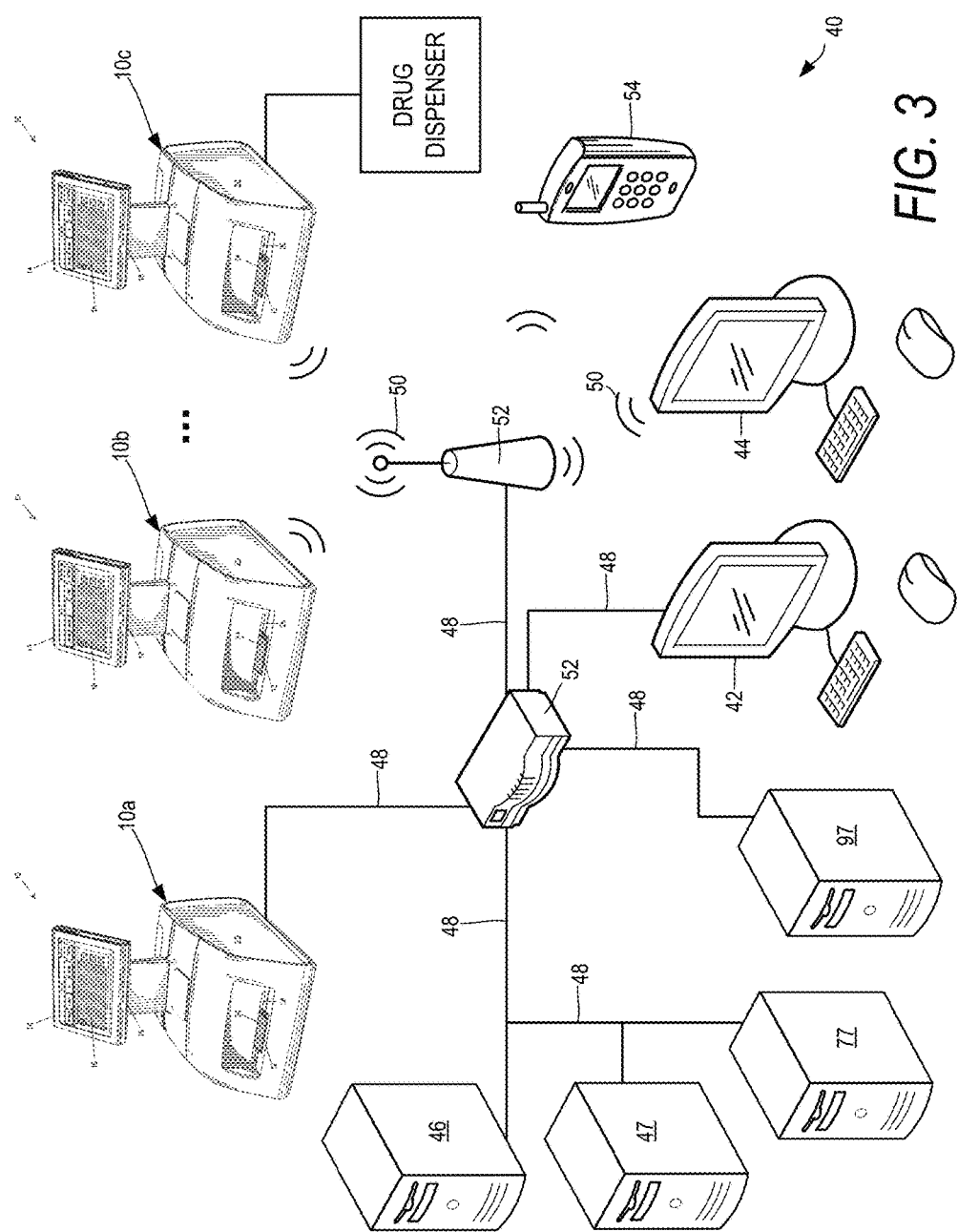
FIG. 3 shows an illustrative embodiment of a medical labeling network arrangement at a medical facility.

A network adaptor 38 is operatively connected to communicate with the processing component 22 for translating signals received by the computer terminal 10 over a network 40 at a medical facility, such as that illustrated in FIG. 3. The network adaptor 38 can be compatible with any type of network communication. For example, the network adaptor 38 can include a hardwired, 10Base-T, 100Base-T, or 1000Base-T Ethernet interface with an RJ-45 socket, a coaxial cable interface, a fiber-optic interface, any format of wireless communication interface such as an antenna compatible with any of the 802.11 standards established by the IEEE, or any combination thereof. Embodiments including wireless network adaptors 38 can employ any desired securing protocol such as WEP, WPA and WPA2, for example, and other suitable security protocol. For embodiments including a network adaptor 38 compatible to communicate over a plurality of different network communication channels, both a hard-wired communication portion of the network adaptor 38 and a wireless communication portion of the network adaptor 38 can optionally be concurrently active. Thus, the computer terminal 10 can optionally communicate via both the hard-wired and wireless portions of the network adaptor 38 concurrently.

As shown in FIG. 3, a plurality of the computer terminals, each referred to generally at 10 and separately at 10a, 10b, 10c, can be included in a network 40 at a healthcare facility. For example, each operating room in which surgical procedures take place may have one of the computer terminals 10 located therein. Other networks may include a computer terminal 10 in an examination room where procedures such as minimally invasive examinations of patients are conducted.

The network 40 also includes a pharmacy computer terminal 42 executing computer-executable instructions (referred to hereinafter as an administration tool or "AT") that, when executed, manage one or more, and optionally all of the computer terminals 10. Each computer terminal 10 to be managed by the AT can be optionally assigned a user-specified designation using the AT to distinguish the computer terminals from each other on the network 40, and to optionally provide the user with a brief description of each computer terminal 10. For example, a computer terminal 10 located in operating room #1 can be assigned the designation OR-1 to indicate its location. According to alternate embodiments, the user-specified name Cart-1 could be assigned to a computer terminal on mobile cart #1. An IT computer terminal 44 can also optionally be connected as part of the network 40 to execute the AT and allow technical personnel to manage technical aspects of the computer terminals 10, but optionally exclude from the permissions granted to technical personnel the ability to alter drug or other medical-related content stored by the computer terminals 10. The permissions granted to a user at the terminals 42, 44 can optionally be determined when the user logs in based on a username/password combination, a computer-readable identification, or any other identifying information. Thus, the terminals 42, 44 do not necessarily have to be dedicated solely for any particular purpose.

The pharmacy terminal 42 can be located in a pharmacy at a healthcare facility, where an inventory of controlled drugs and medicinal substances (hereinafter generally referred to as "drugs") is maintained. A pharmacist or a plurality of pharmacists maintain and administer a master drug database ("MDD") containing an identity, identification code (e.g., NDC) number, concentration and other pertinent information for drugs used by the pharmacy. Drugs are entered into the MDD by the pharmacist, and the terminals 42, 44, and optionally other terminals connected to the network 40 can restrict access to the MDD and prevent unauthorized individuals from entering or altering drug entries in the MDD, and optionally from accessing the MDD altogether. In other words, the pharmacist(s) registered and authorized to work at the health care facility and those they grant permission to access the MDD are the only individuals permitted to manipulate data in the MDD.

From the MDD, the pharmacist manages a formulary to be stored in the memory 24 of one or more of the computer terminals 10 using the AT with the pharmacist permission. The formulary can include a subset of the MDD, and the subset can optionally comprise drugs that are commonly used in the operating room or other locations at the healthcare facility where the computer terminal 10 is positioned. The same formulary can optionally be stored in the memory 24 of more than one computer terminal, and can optionally be customized to include drugs utilized during surgical procedures relating to a particular medical discipline. For example, the same formulary comprising drugs commonly used during cardiac surgical procedures may be stored in the memory 24 of computer terminals 10a, 10b, which are each located in a respective operating room dedicated for such procedures. Another, different formulary comprising drugs, optionally in appropriate doses, suitable to be administered to children can be stored in the memory 24 of a computer terminal 10 located in an operating room dedicated for pediatric surgical procedures. According to alternate embodiments, the formulary 36 stored in the memory 24 of a computer terminal 10 can be evaluated and updated, replaced or otherwise changed before each surgical procedure if the operating room where the computer terminal 10 is located is not dedicated for a particular type of surgical procedure. When a formulary update is needed to accommodate a specific type of procedure, a pharmacist's access can be required to update, replace or otherwise change the formulary in the computer terminals 10, and updating, replacing and changing the formulary in the memory 24 in each of the computer terminals 10 can be performed over the network as described in detail below.

In addition to a pharmacist's level of permission, there can be other permission levels limiting access to the computer terminals 10 to different users. For example, an anesthesiologist may be granted permission to use a computer terminal 10 to interrogate a barcode or other machine-readable code on a drug vial to extract the identity of the drug and print a label to be applied onto a syringe. The anesthesiologist can optionally also be granted permission to confirm that the interrogation of a barcode has returned the proper drug identification. However, the anesthesiologist may be prevented from editing the formulary stored in the memory 24 of the computer terminal 10.

Additionally, an IT professional can be granted permission to address any technical, computer hardware-and-software-related issues with the computer terminals 10 that are unrelated to the specific drug information of the MDD and/or formulary. For example, the IT professional may be granted permission to assign and/or change: an IP address of the computer terminals 10, a security protocol employed, and other computer-specific matters. However, some information related to the formulary such as the version and description of the formulary can be viewed by the IT professional to ensure that the proper computer terminal 10 has the correct formulary installation. This also applies to version and description information of the operating system, BIOS 28, configuration data 32 and administration instructions 30.

The network 40 in FIG. 3 also includes an email server 46 through which email is to be transmitted to individuals who perform tasks related to the computer terminals 10 at the healthcare facility. The email server 46, like the computer terminals 10, and optionally other resources of the network 40, can transmit signals to other network resources via hard-wired communication channels (represented by solid lines 48 in FIG. 3) such as CAT-5 Ethernet cable, via wireless communication channels (represented by arched, radiating signals 50), or a combination thereof. For example, email messages notifying individuals that a triggering event has occurred on one or more computer terminals 10 are transmitted from the email server 46 to one or more of the terminals 42, 44, a portable communication device 54 such as a personal digital assistant, cellular telephone, tablet or laptop computer, and the like. Additionally, the email server 46 can be configured to apply one or more rules that organize and deliver the information in more meaningful ways to the user. For example, a pharmacist may want notification of all problems with the formulary 36 (e.g., a "drug not found" notification) to be aggregated together and delivered to him at the start of his work shift and again 4 hours later. The email server 46 can be configured to transmit such notices in a single communication to the pharmacist at those times. Further, different pharmacists may prefer different notification procedures and different times at which such notifications are to be received, and the email server 46 can optionally be configured to satisfy the requests of each pharmacist individually. However, a group of IT technicians may want prompt notification of technical problems that prevent a computer terminal 10 from operating properly in a surgical suite. Again, the email server 46 can be configured to promptly transmit such notifications to the IT technicians substantially immediately upon detecting such technical problems.

Network resource allocation equipment 52 such as switches, routers, wireless access points, and the like can be included in the network 40 to share network resources and establish communication between the computer terminals 10 and the terminals 42, 44. Additionally, the computer terminals 10 can optionally serve as an expansion port to which other network resources such as the automated drug dispensing system 56, commonly referred to as a "smart cart", can be connected to the network to dispense and document the strength, quantity and type of drug according to a schedule or in response to the occurrence of a predetermined event. Additionally, since one of the functions of smart carts is to control the dispensing of drugs and one of the functions of computer terminal 10 is producing labels for containers such as syringes that are filled with drugs from the smart cart, there are benefits related to efficiency if the devices can share information. For example, a network connection between the smart cart and computer terminal 10 will allow user login information such as username and password entered on one device to be shared with the other device so a user is authenticated on both devices with a single login. Other benefits include being able to share information about drugs being used in a procedure between the devices so verification and reconciliation of drugs can be performed to ensure the proper medications are dispensed, labeled and tracked for improving the accuracy of patient records and accurate billing. As shown in FIG. 3, the automated drug dispensing system 56 is hard-wired to the computer terminal 10c, which is connected wirelessly to other network resources.

Before the computer terminals 10 are usable in a medical environment, the AT software can be installed on one or more of the terminals 42, 44 to be used by a pharmacist at a hospital or other health care facility to populate the MDD. The AT accepts drug information from various sources such as commercially available drug databases (e.g. Lexicomp) and allows the pharmacist to selectively add drugs to the MDD, which can be stored at network-accessible storage server or locally by the terminal 42, 44 running the AT. In simplest terms, the MDD is the set of drugs available to the hospital or other healthcare facility.

Once the MDD is populated with drug information, the pharmacist will use the AT to select a subset of drugs from the MDD to be added to the formulary that will be stored in the memory of one or more of the computer terminals 10, thereby enabling the computer terminals 10 to recognize the drugs in that formulary. The formulary managed using the AT running on one of the terminals 42, 44, as it pertains to the computer terminals 10, can be considered an official set of medications with associated information for preparing and labeling drug containers in accordance with a medical labeling standard. The "associated information" can include information for preparing the drug, which usually means diluting the drug when needed. It can also include information related to the color, patterns, graphics and textual information printed on the label for specific drugs to render those labels, once printed, compliant with the medical labeling standard. Other types of associated information can be files, data for implementing a computer-generated voice, references to files for audibly pronouncing the name of the drug and important drug related information such as the concentration value and concentration units, or any combination thereof. For example, in the case of Propofol 10 mg/ml, a single audio file, or more than one audio file or references to audio files can be combined together to audibly speak the drug name and concentration of the drug as "Propofol ten milligrams per milliliter". According to the present example, the drug name "Propofol" can be contained in one audible file while the concentration value "ten" is in another audible file and the concentration units "milligrams per milliliter" in a third audible file. These three audio files can be executed and played in sequence to allow the computer terminal to audibly broadcast "Propofol ten milligrams per milliliter" via the speaker 17 in response to the scanning of a barcode associated with the container that contains 10 mg/ml Propofol. Other audible information including information about errors such as "do not use drug", for example, can also be associated with a drug in the formulary using the AT. The "do not use drug" audible information can optionally be audibly output using the speaker 17 when a drug has been recalled and a pharmacist wants the computer terminals 10 to notify users not to use a drug that has been recalled, or is otherwise not suitable for use, for example. The computer terminal 10 can automatically assign some audible drug information by examination of the data related to the drug. For example, the concentration value 10 can be used to select the audible file or file reference that speaks the word "ten". The same applies to the concentration units. mg/ml can automatically be used to select the audible file or file reference corresponding to "milligrams per milliliter". Since the MDD can include information on many types of drugs used in the hospital including pills, capsules, ointments, patches, injectables, etc., the pharmacist can optionally select only the drugs from the MDD that are commonly used by anesthesiologists in the operating room (interchangeably referred to herein as the "OR") for a particular procedure or other points of care in the facility where drug containers are labeled prior to dispensing to patients. These are usually the injectable drugs. This subset of drugs can optionally be further narrowed into application-specific sets for pediatrics, etc. . . . . .

Once the pharmacist selects the drugs for the formulary and assigns the associated information to each drug, a formulary "package" is created. This package is a single electronic file containing all formulary information in a format suitable for delivery to the computer terminals 10 on which the formulary is to be stored. Assembling the formulary into a single package simplifies the transfer of information from the terminal operating the AT to the intended computer terminals 10. It also ensures that all information for that version of the formulary to be transferred to the computer terminals 10 is encapsulated in a single file so no information is lost or forgotten. The formulary package is then transmitted over the network 40 to the computer terminals 10 intended to receive the formulary package, as selected using the AT. According to alternate embodiments, the formulary package can optionally be stored on a USB flash drive and delivered to the computer terminals 10 by plugging the USB flash drive into the computer terminals 10 that are to receive the formulary package, which is then automatically installed. This makes the transfer an all-or-nothing proposition, meaning that the existing formulary on the computer terminals 10 is completely replaced by the formulary package being transferred. If the received formulary package is incomplete or corrupt, it will not be able to be installed on the computer terminals 10, and the user will be alerted to the installation failure.

In addition to delivering formulary packages, the computer terminals 10 accept other types of packages for configuration and software updates. Any of these packages can be delivered via USB drive or network. All packages are encoded with a digital signature to prevent the contents of the package being altered or corrupted. Additionally, the USB flash drive can optionally be required to possess a predetermined digital signature to ensure that only authorized USB flash drives can be plugged into the computer terminals 10 to install a formulary, configuration or software update package.

For example, a configuration package 32 stored in the memory of the computer terminals 10 controls the behavior of those computer terminals 10 when preparing and labeling syringes. It is can be used to enable or disable features of the computer terminals 10 such as requiring verification that the drug information displayed on touch-screen display 14 matches the drug container scanned by scanner 18 before printing the label. A pharmacist, head of anesthesia or other authorized individual can customize the workflow to dictate how syringe preparation will be handled and use the configuration package to cause the computer terminals 10 to conform to that desired. Once the configuration package is installed, the computer terminals 10 can impose that workflow on the user (e.g., requiring an authorized confirmation). Multiple workflows can be installed on any given computer terminal 10. In some cases, a user can be granted permission to select a workflow for their use on computer terminal 10. A workflow can optionally be selected based on a user's login information. This allows different workflows for different users. For example, a new resident in the anesthesia program may have all extra verification enabled while a senior physician may have a different workflow configuration. Each workflow can define a sequence of actions to be performed, and optionally is required to be performed, by a user when interacting with the computer terminals 10.

From time to time the software such as the operating system on the computer terminals 10 may need to be updated and/or upgraded. A software update package from a proprietor of the computer terminals 10 may be created and transmitted on a USB flash drive, CD, and/or over a communication network to a hospital for installation on the computer terminals 10, which may change or improve the operation of the system.

Each formulary, configuration and software update package has an identifier string and version number. The identifier can provide human readable information that describes the contents of the package (e.g. Pediatric formulary). A unique version number is assigned to formularies and configuration packages automatically by the AT or from the vendor in the case of software update packages. The combination of the identifier string and version number makes each package easy to identify and track. The computer terminals 10 can display this information on the touch-screen display 14 or send it over the network 40 for remote monitoring. This is useful for tracking which systems have been updated and which system have not.

As described above, a plurality of different formularies may be needed for different purposes. One formulary may contain drugs for general adult surgeries while another may contain different drugs or preparations (dilutions) for pediatric procedures. The AT allows multiple formularies to be created and managed from a single MDD. The user interface of the AT that controls the deployment of formulary packages over the network 40 allows the user to select a single computer terminal 10, as might be required for testing a new version of a formulary before wide-scale deployment, or a plurality or all of the computer terminals 10. In the case of multiple computer terminals 10, these can be manually selected or pre-assigned in groups so all computer terminals 10 in a group can receive the same formulary.

Related to the installation of packages such as formularies, a distribution list of authorized computer terminals 10 can optionally be encoded with the formulary package or other packages such as the configuration package or software update package. The distribution list defines which computer terminals 10 are allowed to install the package. A computer terminal 10 checks the distribution list before installing the package to see if it is on the list. If the computer terminal 10 is not on the distribution list, the package will not be installed. In other words, rather than individually selecting the computer terminals 10 using the AT to which the package is to be transmitted, the computer terminals 10 that are intended to receive each package can be included in the distribution list in the packages themselves. The packages can then be transmitted via the network to all computer terminals 10, but installed on only those computer terminals 10 included on the distribution list. This is particularly useful when a facility uses USB flash drives to distribute packages, but can also apply to network installed packages. For example, a USB flash drive containing a formulary package for general adult surgery might be inadvertently be plugged into a computer terminal 10 intended for pediatric use. The distribution list embedded in the package prevents the pediatric computer terminal 10 from installing the formulary package for the general adult surgery onto the computer terminal 10 intended for pediatric use.

Each computer terminal 10 can optionally be limited to store a single formulary at a time, but alternate embodiments can allow a plurality of different formularies to be installed and selected by the user as the user logs into the computer terminal 10. Alternately, a formulary could be tied to, and automatically selected as the active formulary based on the login information of the user when that user logs in. This would allow a Gastroenterologist, for example, to recognize a different set of drugs with the computer terminals 10 for minor procedures than an anesthesiologist for general surgeries.

In another embodiment, a single formulary 36 can contain drug information suitable for multiple types of procedures such as pediatric, cardiac, general surgery, gastroenterology, minimally invasive surgery and others in a single formulary. The user of computer terminal 10 can select the type of procedure being performed. The type of procedure selected would correspond to a specific subset of drugs and associated drug information contained in formulary 36. For example, a specific drug may not require dilution when used in typical adult surgeries, but may require dilution in pediatric procedures. A single formulary can have different information for preparing the same drug based on the type of procedure currently selected. Additionally, configuration data 32 can be used to limit the procedure types available to a particular user. For example, an anesthesiologist may have full access to all procedures, but a gastroenterologist may be limited to drugs suitable for procedures such as colonoscopies.

Related to a single formulary containing drug information for multiple types of procedures, a default selection of the procedure type can be made based on the user login information on computer terminal 10.

When packages are deployed to the computer terminals 10 over the network, options can be specified that determine when the packages will be installed. It is undesirable to cause a package to be installed in the middle of a medical procedure, so options to defer package installation until the user logs out of the computer terminal 10, or after a specific time, such as 10 PM, or a combination of options such as the first time no user is logged in to the computer terminal 10 and the time is after 10 PM. Other options such as install on next reboot are also possibilities. An optional time delay can be specified that will not immediately install a package when a user logs out. This is to handle the case where one physician goes on break during a long procedure and another physician fills in for the physician on break. In this case, a logout may be followed by another login because the procedure is still underway. A reasonable delay is needed to ensure another user is not going to login. This can also be accomplished by displaying a warning message on the touch-screen display 14 that a package is about to install and a delay to allow the user to touch the screen to defer the installation, providing enough time and notification for the user to log into the computer terminal 10.

Each computer terminal 10 is designed to operate autonomously. Once it is has a formulary and configuration package installed, the computer terminals 10 will operate with or without a network connection. This ensures the device will continue to work and not interfere with the medical procedure even if the network connection stops functioning. While the network is not functioning the computer terminals 10 will store information that needs to be transmitted for logging, record keeping, billing, and other purposes when the network connection is re-established.

When the computer terminals 10 are connected to the network 40 and the network connection is functioning properly, they can perform other functions in addition to receiving packages. For example, the computer terminals 10 can transmit information regarding the status of the: hardware (e.g., the printer 26 is low or out of a particular printing ink or toner, the printer is out of label stock), package information such as versions of packages installed, the user logged into each of the computer terminals 10 (if any), important events such as "drug not found" alert in response to scanning a barcode with the scanner 18, for example, which may indicate a drug is in the hospital that was not included in the formulary on that computer terminal 10 and may not be properly usable, etc. In such situations, an alert signal is transmitted by the afflicted computer terminal(s) 10 to the email server 46, and the email server 46 responds by composing the email or other message containing textual information corresponding to the alert signal and transmitting the email or other message to the intended recipient. The status information can optionally be transmitted by the computer terminals 10 automatically, not in response to receiving a status request, upon the occurrence of an event, periodically, when a status changes, or a combination thereof. According to an alternate embodiment, the AT running on the terminal 42 or 44 can be used to access the computer terminals 10 over the network 40 to determine the status of each computer terminal 10, the various components making up the computer terminals 10, or other information regarding the computer terminal 10. Thus, the AT running on the terminal 42 or 44 can be used to receive status report information autonomously transmitted by the computer terminals 10, and/or can be used to retrieve (or request transmittal of) the status report information from the computer terminals 10. The status report information can optionally be tabulated by the AT running on the terminal 42 or 44 and presented in a logical manner to the user, thereby allowing the user to readily identify any of the computer terminals 10 that are not operating as intended.

In another embodiment, event information that occurs on a computer terminal 10 can be shared with other computer terminals 10 on the network 40 either through the AT running on one or more of the terminals 42, 44, or the email server 46, or with a dedicated software program on the network 42, or directly with other computer terminals 10 on the network 42. Shared information can be used to optimize the workflow of the users by sharing events such as first time verification of a drug being used at a computer terminal 10 so other users will have the benefit of the drug verification and not have to perform the same verification procedure on each computer terminal 10.

Related to the aforementioned sharing of information between computer terminals 10 on the network 40, a syringe or other container labeled by the computer terminal 10 can include a unique identifier in a machine-readable format on the label. For example, a unique serial number could be assigned to each syringe and encoded in a barcode that is applied to the syringe. Information related to the unique identifier numbers of the containers prepared at a particular computer terminal 10 and information about the drug in the container (e.g., drug name, concentration, expiration date and/or time, other information, and any combination thereof) can be shared with other computer terminals 10 on the network 40 so a container that is prepared for one patient but is moved to another operating room can be verified when the machine-readable code is scanned by the scanner of the computer terminal 10 in the other operating room. As a result of scanning the barcode or other machine-readable code, a notification can be provided to the user, alerting the user that the drug within that drug container is not intended for that patient (i.e., it is intended for the patient in the original operating room). Alternately, for drug containers permitted to be moved between operating rooms, the contents of the container can be verified in each operating room, and whether the contents are expired, by scanning the machine-readable code with the scanner 18 provided in each of those operating rooms.

Messages of importance to users such planned updates to software, formularies, configuration changes or even messages such as staff meetings or departmental messages can be sent out over the network 40 from an AT running on terminals 42, 44 to one or more computer terminal 10 systems on the network and displayed on the touch-screen display 14 when the user logs into the system. If the message is received on a computer terminal 10 while a user is logged in, a non-intrusive message will notify the user that a message is waiting to be displayed. This will prevent any interruption of the user in the middle of a medical procedure. Messages can be configured to display once per user or each time a user logs in until the message is discontinued from the terminal(s) 42, 44 running the AT. Authority to send out or discontinue messages can optionally be granted or restricted to specific users of the AT.

The usefulness and effectiveness of computer terminal 10 can be enhanced by associating patient information with a medical procedure. Patient information at a healthcare facility is usually stored on an Electronic Medical Record (EMR) system. The EMR typically collects and manages patient Personal Health Records (PHR) from sources throughout the healthcare facility and makes those records available to authorized users and equipment through the network. As related to computer terminals 10, patient information can be transmitted over the network 40 to one or more of the computer terminals 10 from an EMR system in the healthcare facility using HL7 or another healthcare specific network protocol. Patient information such as patient name, ID, date of birth, sex, medical conditions, drug history and other relevant information from the EMR is received and stored by an EMR gateway server. The EMR gateway server can collect and aggregate patient information received from the EMR when the EMR transmits information over the network 40. In other words, the EMR gateway server receives information such as ADT (admission-discharge-transfer) codes and other HL7 messages transmitted from the EMR to different devices intended for different recipients over the network 40. Each such transmission from a plurality of different EMR servers can optionally be collected and recorded by one common gateway server or a plurality of gateway servers. Thus, the information collected by the EMR gateway server can be accessed and retrieved from the EMR gateway server rather than from the EMR server. Since patient information is often transmitted on the network from the EMR as it becomes available from different sources in the healthcare facility, it is necessary to collect and combine the patient information so the appropriate information it is available for a specific purpose. The EMR gateway server performs this function for the computer terminals 10. The EMR gateway server can also reduce the cost of connectivity to the EMR because many EMR systems have a fee per connection and it can be less expensive to connect one EMR gateway server to the EMR than many individual computer terminal 10 systems. An EMR, an EMR in combination with an EMR gateway server, and a plurality of EMR systems in network communication with a common EMR gateway server are represented generally at 47 in FIG. 3. Patient information is transmitted from the EMR gateway server 47 on network 40 to computer terminals 10 when a specific patient identity is entered into a computer terminal 10 or requested from a computer terminal 10 before the patient that is to receive medical attention at a location, such as in an operating room of a healthcare facility, in a pharmacy, or other desired location, for example, where the computer terminal 10 is located. The specific patient's identity can be selected from a patient list stored by the EMR gateway server 47 and accessed using the computer terminal 10, or determined in response to the user entering unique patient identification information such as a patient ID using touch-screen display 14 or scanner 18, for example. The patient ID or other patient-related information can be transmitted over the network and used to look up the patient information from the EMR gateway server. The patient information received from the EMR gateway server by computer terminal 10 is verified by the user using touch-screen display 14 and stored in memory 24 for the duration of the procedure. Likewise, the user can enter, or select from a list displayed via the display 14, the specific procedure to be performed, which is stored in the memory 24 and associated with the patient information. The procedure can optionally also be transmitted from the computer terminal 10 over the network 40 to be stored in association with an entry for that patient in the EMR gateway.

Patient information related to drug allergies, other drugs the patient is taking and relevant information such as date of birth, sex, weight, etc. can affect the selection of medications and doses administered during a medical procedure. Patient information can be associated with a procedure on computer terminal 10 as described above. In the simplest use case, the patient information locally stored in memory 24 on the computer terminal 10 can be displayed on touch-screen display 14 for review by the user. In more complex implementations, the patient information in memory 24 can be accessed by the processing component 22 of the computer terminal 10 and checked as drugs are being prepared on computer terminal 10 to provide warnings to the user if a drug(s) being prepared and labeled is not suitable, or is not apparently suitable to be administered to the patient based on the patient information available. Based on the patient information, information in the formulary, the procedure identified by the user, or any combination thereof, other analyses can be performed, such as verification that the formulary or type of procedure selected as described above or gleaned from the content of a formulary tailored for a particular patient/surgical procedure is appropriate for this patient, patient drug allergies, drug to drug interactions, age related medication restrictions, etc. While performing such an analysis on the computer terminal 10 is one option, a more sophisticated analysis may be possible by communicating with a server included as part of the network 40 that receives individual requests for drug verification along with an indication for selecting the appropriate patient information from the computer terminal 10 and transmits a response to the computer terminal 10 that approves the use of the drug or provides the user with an appropriate warning that is displayed on touch-screen display 14.

Patient information associated with a procedure on computer terminal 10 as described above, can be used to provide drug tracking information for billing and patient records. As drugs are being prepared on computer terminal 10, the drug related information can be transmitted along with information required to associate the drug information with a patient to the EMR gateway server 47. The EMR gateway server 47 then transmits the drug related information along with associated patient information to the EMR 47 at the facility over network 40 using HL7 or another healthcare specific network protocol compatible with the EMR 47.

In another embodiment, the Patient information associated with a procedure on computer terminal 10 as described above, can be used to transmit information to a LIS (Laboratory Information System) 97 in the facility, shown in FIG. 3. The LIS 97 includes a network connected storage device such as a database server for example, that stores records of laboratory samples that are to be, or have been, subjected to medical testing at the laboratory in a computer-readable medium. In many surgical procedures, it is common to have a specimen removed from the patient that is sent to the laboratory for analysis. The specimen is often labeled by hand with patient information, tissue information, site information, date and time of extraction, attending physician, etc., and sent to the laboratory. The computer terminal 10 can allow the user to print a label with the same information that would normally be written by hand and transmit an electronic record of the data to the LIS 97 for storage, so the information on the label of the specimen will exactly match the information stored by the LIS 97 when the specimen arrives in the laboratory.

The computer terminals 10 can transmit data over the network to one or more of the terminals 42, 44 running the AT, a network-connected server, or other network resource, for example, that can be used to generate and analyze drug usage patterns based on procedure type, user or other relevant parameters. As drugs are being prepared by the user using a computer terminal 10, information about the drug including the drug name, concentration, container ID, date, time, user and procedure information can be stored in memory 24 on computer terminal 10 and then transmitted to the terminal(s) running the AT or a dedicated server. The information can then be post processed to extract the required information for determining usage patterns of drugs.

AIMS (Anesthesia Information Management Systems), also known as ARKS (Anesthesia Record Keeping Systems), includes a server, represented generally at 77 in FIG. 3, that receives and stores drug usage information for each patient during a medical procedure to allow anesthesiologists to electronically record patient vital signs, drugs administered, important events that occurred during the surgery and other relevant information related to anesthesia administration and monitoring during a procedure. Many AIMS systems are programmed with a set of all drugs that could be administered in the operating room. This can be hundreds of drugs. When recording a drug in the AIMS 77, the user of the AIMS 77 usually navigates through multiple levels of menus to find the correct drug. A more efficient and accurate method of drug selection can be implemented using network 40 and computer terminal 10 to transfer drug information as they are prepared to the AIMS 77. The AIMS 77 user would then be presented with a short list of the drugs prepared on the computer terminal 10 when they record drug information on the AIMS 77. If the drug is not found on the short list of drugs prepared on computer terminal 10, then the user would have the option to access the full list of drugs stored on the AIMS 77. Although the email server 46, EMR 47, AIMS 77 and LIS 97 appear in FIG. 3 as separate, distributed computational platforms, it is to be understood that one or more of such platforms can be combined and embodied on a single computational platform without departing from the scope of the present invention.

Computer terminal 10 can optionally include a speaker 17 that plays audio files in response to the scanning of a barcode on a drug container by the scanner 18 during preparation of a label. Computer terminal 10 stores audio files or files that can be used to create audible sounds in memory 24. These audio files are executed by the computer terminal 10 to "speak" a drug name and concentration from the speaker 17 when a user scans a drug container using scanner 18. This provides audible confirmation to the user of the drug that was scanned. Other devices on the network that want to provide audible output of drug names, concentrations values and concentration units can transmit a message to computer terminal 10 over the network using a defined interface and message format to instruct computer terminal 10 to audibly "speak" the specified drug name and concentration information. The message can optionally include volume information. Alternately, the other device can transmit a message to computer terminal 10 using a defined interface and message format to select and receive the sound files from the computer terminal 10 and play the sound files locally on the device.

In another embodiment, the computer terminal 10 can transmit a list of prepared drug information over the network 40 to an administration terminal that is mounted near the point of drug administration to the patient. The administration terminal (not shown) can include a scanner similar to scanner 18 provided to the computer terminal 10, a display device for displaying the results of scanning a barcode or other machine-readable code, a processing component for converting a scanned code to the identity of the content of the container labeled with the barcode, and a network adaptor to receive the list of prepared drug information over the network. Optionally, the administration terminal can also include a speaker to audibly output the information pertaining to the content of the container labeled with the barcode when the barcode is scanned. The display device and/or the speaker can also optionally output a warning about the container and/or the drug therein in response to reading the barcode and determining that a warning is warranted.

Figure 6:
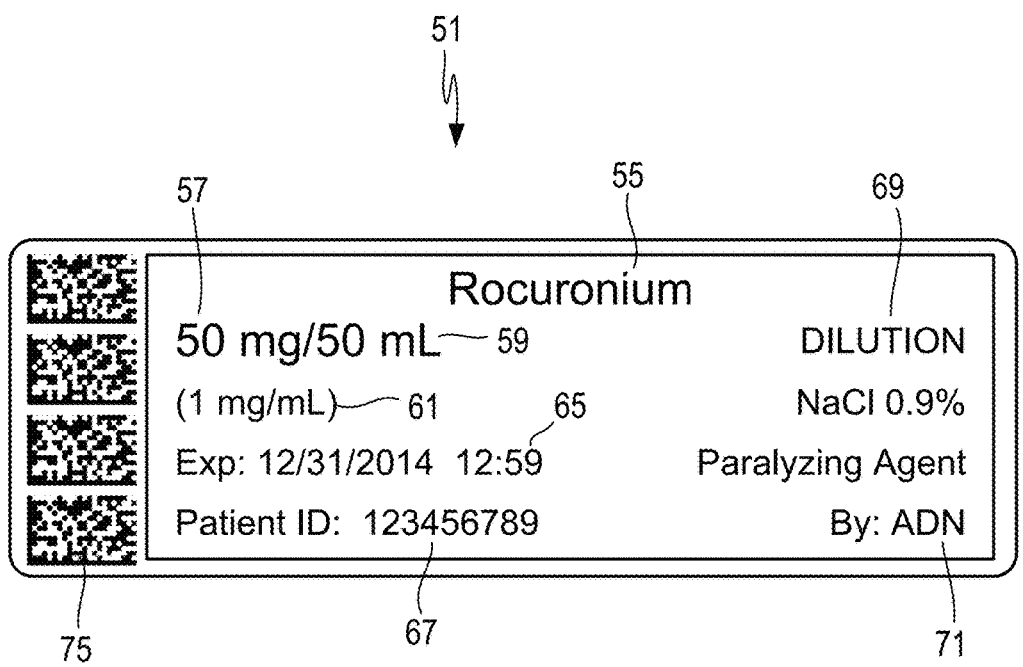
FIG. 6 shows an illustrative embodiment of a label printed in accordance with the present disclosure.

Regardless of its purpose, an illustrative example of such a label 51 is shown in FIG. 6. As shown, the label 51 produced by the computer terminal 10 can be applied to a syringe or other drug container in which a drug to be administered to a patient can be stored. includes human readable information identifying at least one of: a drug name 55, a total dose 57, a total volume 59, a concentration 61, expiration information 65, a patient ID 67, dilution information 69, and information 71 identifying a person who prepared the label 51. One, or a plurality of different or redundant computer-readable codes 75 are also printed on the label 51, such as a barcode for example. The code(s) 75 can be redundant to encode the same information, or different to encode diverse information (e.g., a first one of the codes 75 can encode the drug identity or other drug-specific information, and a second one of the codes can encode the patient identity or other patient-specific information) to allow a user to scan the code(s) 75 on the label 51 to retrieve any of the encoded information.

Figures 4, 5:
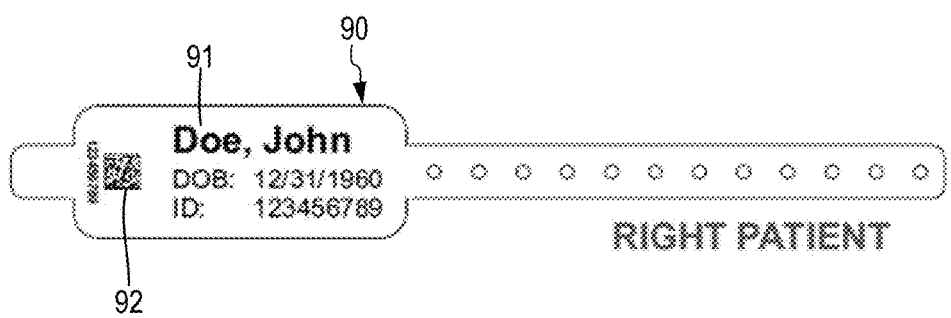
FIG. 4 shows an illustrative embodiment of a prescription form prescribing a drug to a patient, the prescription form comprising a computer-readable code identifying the patient.
FIG. 5 shows an illustrative embodiment of a wristband worn by a patient and including a barcode encoding information indicative of the patient's identity.

FIG. 4 shows an illustrative embodiment of a computer-accessible source of patient information depicted as a prescription form 80 prescribing a drug to a patient. Although shown as a hardcopy prescription form 80, the computer-accessible source can be any source of patient information that facilitates the automated input of the patient information into the computer terminal 10 other than through manual, human entry of individual keystrokes for each character of the patient's name, identification number, etc . . . , which is prone to human error. In other words, the information indicative of the patient's identity, such as the patient's name, identification number, and the like, can be encoded by a computer-readable code 81, also referred to as a patient code 81, provided to the prescription form 80. The encoded information can be obtained by the computer terminal 10 by scanning the computer-readable code 81, and without relying on the manual entry of such information by a user, or without the risk of human error being introduced during entry of the patient information via the computer-readable code 81.

Although shown as a prescription form 80, other examples of the computer-accessible source include, but are not limited to a patient's chart with a patient code 81, a sticker bearing a patient code 81 applied to the patient's chart or other paperwork, an electronic order transmitted to the computer terminal 10 electronically, as a communication over the communication network 40 from the EMR gateway server 47 or other repository of patient information accessible to the computer terminal 10, or any other source of the patient information to be encoded. However, the patient code 81 can optionally be independent of the patient, or article worn by the patient that is scanned to identify the patient to a medical device such as an infusion pump or other drug deliver device that administers a drug to a patient in controlled quantities an automated manner according to delivery parameters programmed into the device. In other words, the patient code 81 or other computer-accessible source can be any source that can be used to communicate the information indicative of the patient's identity to the computer terminal 10 other than a computer-accessible source that will be used to determine the patient's identity for confirmation purposes when the drug is to be administered. As discussed in detail below, utilizing a computer-accessible source that is independent of the patient or article worn or otherwise associated with the patient and that is used to program a medication delivery device, for example, to obtain the patient's information to be applied to the label 51 allows for confirmation of the patient's identity at a time when the drug is to be administered by the medication delivery device. For example, FIG. 5 shows an illustrative embodiment of a wristband 90 to be worn by a patient admitted to a hospital or other healthcare facility. In addition to human-readable information 91 concerning the patient, the wristband 90 also includes a barcode 92 or other computer-readable code encoding information indicative of the patient's identity. Since the wristband 90 is worn by the patient, and the barcode 92 is scanned by a clinician to identify the patient during medical treatment, such a barcode 92 would not be considered a computer-accessible source of patient information that is independent of the patient. In contrast, if the barcode 92 is scanned as the computer-accessible source as described herein, and this same barcode 92 is also scanned to identify the patient at a time when a drug is to be administered, the patient identity obtained from each source will always match. This scenario could possibly result in an erroneous confirmation of the patient's identity even if the barcode 92 erroneously identified the patient.

As shown in FIG. 4, the prescription form 80 includes a computer-readable code 81 in the form of a two-dimensional barcode encoding information indicative of the patient's identity. The two-dimensional barcode can optionally encode the data itself, or encode a storage location from where the encoded information can be retrieved. The scanner 18 (FIG. 2), in response to reading the computer-readable code 81, transmits a signal indicative of the identity of the patient or other patient-specific information to be received by the processing component 22. In turn, the processing component 22 can generate patient-specific label content, including the barcode 75 encoding information indicative of the patient's identity, to be printed onto the label 51.

The prescription form 80 can also optionally include another computer-readable code 87, which appears in FIG. 4 as a one-dimensional barcode, but can be of any other suitable format compatible for use with legacy equipment that may not be configured to read the patient code 81 encoded as a two-dimensional barcode, for example. Thus, the computer-readable code 87 can optionally be redundant, encoding the same information encoded by the patient code 81, but in a format that is different than the format of the patient code 81 for use by legacy devices that may not be configured to read the most-recently-developed barcodes or other advanced computer-readable codes.

Figure 7:
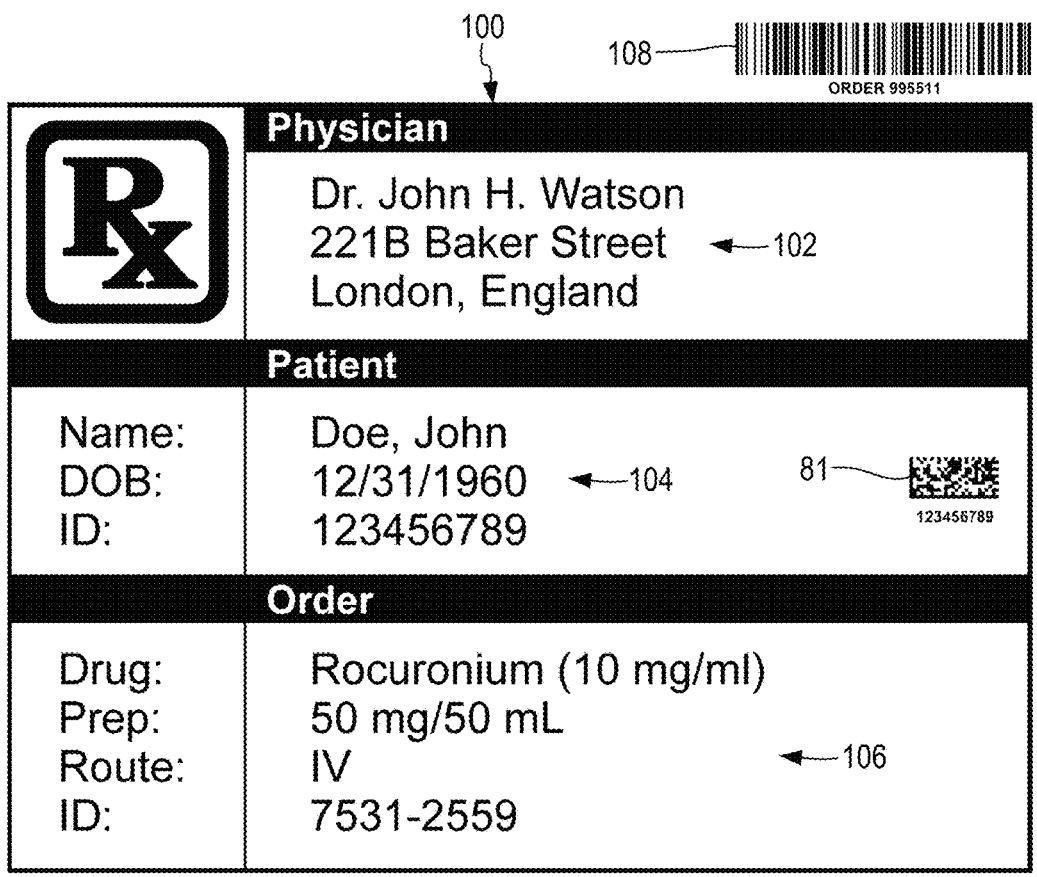
FIG. 7 shows an alternate embodiment of a prescription form prescribing a drug to a patient, the prescription form comprising a computer-readable code identifying the patient and a computer-readable drug order code.

FIG. 7 shows an alternate embodiment of the prescription form 100. Similar to the embodiment shown in FIG. 4, this embodiment of the prescription form 100 includes human readable information such as information relating to the prescribing physician 102, information used to identify the patient 104, and order information 106 concerning the prescribed drug. Further, the prescription form 100 also includes the two-dimensional patient code 81 encoding information 104 indicative of the patient's identity. However, unlike the prescription form 80 shown in FIG. 4, the prescription form 100 also includes a drug order code 108, instead of or in addition to the computer-readable code 87, to uniquely identify the drug order stored in the EMR gateway server or other network-accessible database. A human-readable representation of the patient code 81, computer-readable code 87, and/or drug order code 108 can also optionally be arranged adjacent to their respective barcode. The drug order code 108 can encode a storage location from where the full record of the drug order can be retrieved. Further, the computer terminal 10 can optionally be programmed to retrieve a specific portion, but optionally less than all of the information included in the full record (e.g., the name and/or patient ID number of the patient) for purposes of generating the label content to be printed and encoded along with the drug information by the barcode 75 that is to appear on the label 51. For example, in response to scanning the drug order code 108, the computer terminal 10 can retrieve information included in a specific field (e.g., patient name field and/or a patient identification number field) of an XML or other data-exchange format. Thus, the scanner 18 (FIG. 2) can, in response to reading the computer-readable code 81 and/or the drug order code 108, transmit a signal indicative of the identity of the patient or other patient-specific information to be received by the processing component 22. In turn, the processing component 22 can generate patient-specific label content, including the barcode 75 encoding information indicative of the patient's identity, to be printed onto the label 51.

The information indicative of the patient's identity can include at least one of: the patient's name, the patient's date of birth, patient's sex, patient identification number assigned to the patient at the hospital or other healthcare institution, and the like. This information can then be obtained by scanning the code 75 and compared to analogous information obtained by scanning the barcode 92 as described below for purposes of confirming the patient's identification at a time when the drug is to be administered.

The drug order information received from the EMR gateway server or other network-accessible database using the drug order code 108 can include information related to the configuration and programming of devices such as drug infusion pumps and drug labeling systems. For example, a syringe pump is one type of infusion pump that includes a moveable piston adjusted at a suitable rate to deliver the drug according to the parameters input to program the device to control delivery of the drug contained within a syringe. The drug order information can include at least one of the drug name, drug concentration, drug preparation instructions, drug flow rate to be used when administering the drug to patient using a drug infusion pump, drug delivery duration, prescribing doctor or clinician and other information or instructions that relate to the order including drug selection, preparation, administration and follow-up instructions. Any portion of this drug information can be encoded by the one or more barcodes 75 that the computer terminal 10 is to print as label content onto the label 51. Thus, when a scanner or other code reader provided to the drug infusion pump or other drug delivery device scans the barcode 75, such device can be programmed with the encoded drug information.

A similar barcode or other computer-readable code provided to a drug vial or other storage container from which a dose of a drug is to be prepared can also be read by the scanner 18, which transmits a signal indicative of the drug identity to the processing component 22 in response. The processing component 22 then identifies, from the formulary 36, the identity of the drug corresponding to the scanned computer-readable code. In turn, the processing component 22 generates drug-specific label content, including the same barcode 75 as that described above encoding the information indicative of the patient's identity, or optionally a different one of the barcodes 75 encoding information indicative of the drug's identity, to be printed onto the label 51. The printer 26 can then print the label content including the computer-readable code(s) 75 identifying the specific drug and patient that is to receive the drug onto the label 51 that is to be applied to a syringe or other drug container. Any other desired label content such as that described with reference to FIG. 6 above can also be printed in human-readable form (e.g., alpha/numeric characters) onto the label 51.

According to alternate embodiments, the processing component 22 can optionally be configured to receive an instruction for programming a medication delivery device or other medical device used during the administration of a drug to the patient. For example, the processing component can be programmed to receive a rate at which the drug is to be delivered to the patient, for example. Such information can be encoded by a computer-readable code by the processing component 22, and this computer-readable code is also printed on, or otherwise applied to the label 51 as the same, or one of the different barcodes 75 described above.

Such a label 51 printed by the printer 26 can be applied to a syringe or other drug container. To administer the drug in such a syringe utilizing a syringe pump or other medication delivery device configured to be programmed via a computer-readable code, the clinician can approach the medication deliver device and scan the barcode(s) 75 printed onto the label 51 utilizing a barcode reader provided to the medication delivery device. From the barcode(s) 75, at least one of patient identifying information, drug identifying information and the instruction is obtained by the medication delivery device based on the information encoded by the barcode(s) 75.

The barcode 92 on the wristband 90 worn by the patient that is to receive the drug is also scanned using the barcode reader provided to the medication delivery device. As a precautionary measure, the patient identity determined based on the barcode(s) 75 is compared to the patient identity determined based on the barcode 92 to determine whether the patient identities match. In the event that there is a match, the drug delivery device configures itself into a mode in which the drug is to be administered to the patient. However, if the patient identities do not match, an alert can be issued by the medication delivery device to prompt the clinician to ensure that the drug in the syringe is supposed to be administered to this patient, and the medication deliver device can interfere with, or prevent the administration of the drug until such time that manual confirmation that the drug is intended for this specific patient is entered.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A labeling apparatus that generates a label for labeling a drug container at a healthcare facility, the labeling apparatus comprising:
   a code reader that reads a computer-readable code encoding a drug to be stored by the drug container and transmits a signal indicative of the identity of the drug in response to reading the computer-readable code;
   a non-transitory computer-readable memory that stores a drug formulary comprising a plurality of drug entries;
   a processing component that identifies, from the formulary, the identity of the drug corresponding to the computer-readable code and receives additional information from a computer-accessible source; and
   a printer for printing label content identifying the specific drug onto a label that is to be applied to the drug container, the label content comprising the identity of the drug and the additional information formatted in at least one of: a human-readable form, and encoded by a label code that is computer-readable, wherein
      wherein the computer-accessible source comprises a second computer-readable code encoding the additional information, and the code reader is adapted to read the second computer-readable code from a source independent of a patient and transmit an additional signal indicative of the patient identity that is received by the processing component, the source independent of the patient comprising an identification label that is not used to program a medication delivery device.

2. The labeling apparatus of claim 1 further comprising a network component that receives the additional information as a communication transmitted over a communication network as the computer-accessible source.

3. The labeling apparatus of claim 1, wherein the printer is adapted to print encoded information as a plurality of different barcodes comprising a first barcode that encodes the identity of the drug and a second barcode, which is different than the first barcode, that encodes the additional information.

4. The labeling apparatus of claim 1, wherein the printer is adapted to print encoded information as a common barcode that encodes both the identity of the drug and the additional information.

5. The labeling apparatus of claim 1, wherein the processing component is further configured to receive an instruction for programming a medication delivery device, and the printer prints a label code to encode the instruction.

6. The labeling apparatus of claim 5, wherein the instruction comprises at least a rate at which the drug is to be delivered to a patient.

7. A method of administering a drug to a patient utilizing an automated drug delivery device, the method comprising:
   with a computer-readable code reader, scanning a drug code that is computer-readable and a first patient code that is computer readable, the drug code and the first patient code being associated with a drug container storing the drug to be administered by the automated drug delivery device;
   with the computer-readable code reader, scanning a second patient code that is computer readable and independent of the first patient code;
   comparing a first patient identity determined based on the first patient code to a second patient identity determined based on the second patient code to make a determination whether the first patient identity matches the second patient identity;
   configuring the drug delivery device to administer the drug to the patient in response to making a determination that the first patient identity matches the second patient identity;
   initiating an alert in response to making a determination that the first patient identity does not match the second patient identity; and
   interfering with administration of the drug to the patient in response to making the determination that the first patient identity does not match the second patient identity, wherein interfering with the administration of the drug comprises preventing administration of the drug with the automated drug delivery device until manual confirmation that the drug is to be administered is received by the automated drug delivery device.

8. The method of claim 7, wherein said scanning the drug code and the first patient code comprises using a barcode scanner provided to the drug delivery device to scan a label barcode provided to a label applied to a syringe, and wherein said scanning the second patient code comprises using the barcode scanner to scan a patient barcode provided to the patient.

* * * * *